United States Patent [19]

Esch et al.

[11] 4,205,043
[45] May 27, 1980

[54] HAZARDOUS ATMOSPHERE BADGE

[76] Inventors: Victor H. Esch, 10717 Stanmore Dr., Potomac, Md. 20854; Robert M. Fristrom, 10610 Mantz Rd., Silver Spring, Md. 20403

[21] Appl. No.: 902,963

[22] Filed: May 4, 1978

[51] Int. Cl.² .................... G01N 31/22; A62C 39/02
[52] U.S. Cl. .......................................... 422/56; 73/23; 116/206; 422/58; 422/87
[58] Field of Search .......... 23/253 TP, 254 R, 232 R; 422/55, 56, 58, 87; 73/23; 116/206

[56] References Cited

U.S. PATENT DOCUMENTS

| | | | |
|---|---|---|---|
| 1,891,429 | 12/1932 | Ljunggren | 23/253 TP X |
| 3,002,385 | 10/1961 | Wahl et al. | 23/253 TP UX |
| 3,681,027 | 8/1972 | Smith | 23/254 R X |
| 3,689,224 | 9/1972 | Agnew et al. | 23/254 R X |
| 3,697,227 | 10/1972 | Goldstein et al. | 23/254 R X |
| 3,992,153 | 11/1976 | Ferber et al. | 23/254 R X |

FOREIGN PATENT DOCUMENTS

| | | | |
|---|---|---|---|
| 51-72494 | 6/1976 | Japan | 23/253 TP |
| 314125 | 12/1971 | U.S.S.R. | 23/253 TP |

Primary Examiner—Arnold Turk
Attorney, Agent, or Firm—Cushman, Darby & Cushman

[57] ABSTRACT

An inexpensive badge for detection of dangerous gases wherein a plurality of paper discs impregnated with a color sensitive gas indicator chemical are mounted in alignment with apertures in a plastic substrate by a pressure sensitive tape backing. The front face of the substrate is covered with a further strip of pressure sensitive tape, which is removed to initiate indication of gas dosage by the detector.

5 Claims, 3 Drawing Figures

HAZARDOUS ATMOSPHERE BADGE

BACKGROUND AND SUMMARY OF THE INVENTION

The present invention is related to gas detection devices and in particular to a small, inexpensive dosage badge for determining the exposure of firefighters to toxic gases.

Fire atmospheres to which firefighters are exposed commonly include toxic gas components. For example, many fireman are injured as a result of contact with hydrochloric acid gases formed when polyvinyl resins are burned. Accordingly, it is desirable to be able to detect the presence of toxic gases and monitor the exposure dosage to the gas.

Gas detection apparatus are, in general, well known. Examples of prior art systems are described in the following U.S. Pat. Nos. 2,741,912 (Schultze), 3,067,015 (Lawdermilt), 3,084,658 (Schell), 3,112,998 (Grosskopf), 3,113,842 (Udall), 3,876,378 (Montagnon), 3,884,641 (Kraffczyk, and 3,933,029 (Rabenecker).

In general, the presently available apparatus for sampling fire atmospheres are either too cumbersome, too fragile, or too expensive for generalized field use. For example, the patent to Udall (U.S. Pat. No. 3,113,842) describes a gas detection apparatus comprising an evacuated gas chamber having a constricted portion containing a color sensitive indicator chemical that changes color upon exposure to a particular gas. The detection process is initiated by breaking the tip of the glass chamber. While small, the Udall device requires relatively complex fabrication techniques and is thus relatively expensive. Further, an open glass container is not ideally suited for a field environment. Accordingly, a small and lightweight but rugged and inexpensive, individually worn badge for indicating the exposure dosage to toxic gases is needed.

It is believed that the present invention provides such a small, inexpensive dosage indicator badge. A plurality of discs impregnated with a chemical indicator material, which respond with color changes upon predetermined dosage exposures to various toxic gases, are disposed on plastic substrate. A removable cover sheet, suitably formed of a pressure sensitive tape and including a non-adhesive pull-tab to facilitate removal is disposed on the face of the substrate to enclose the chemical detectors. Dosage monitoring is initiated by pulling the cover sheet off of the substrate to expose the impregnated discs.

The badge is easily fabricated and it is presently estimated that the badges can be constructed for less than $0.25 each. Three concentration badges in accordance with the present invention have been tested, weighing less than 0.02 ounces and only on the order of 1–2 inches by 3–4 inches by 0.02–0.05 inches in dimension. The badge can be mounted by adhesive or by a suitable clip on, for example, a hat or the sleeve of a firefighter. Further, the badge is small enough so that it can be disposed within the face mask of breathing apparatus to provide an indication of any leakage of toxic gases into the system.

It is the primary object of the present invention to provide a simple, inexpensive, reliable hazardous environmental condition indicator. This and other objects of the invention will become clear from an inspection of the detailed description of the invention, and from the appended claims.

DETAILED DESCRIPTION OF THE INVENTION

Figure 1:
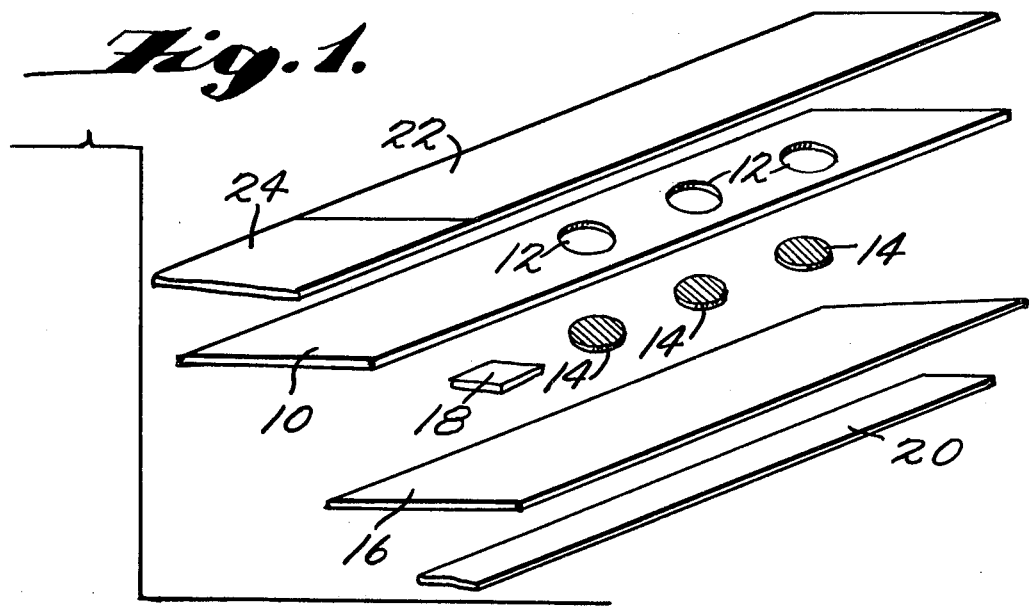
FIG. 1 is an exploded perspective of an exemplary badge according to the present invention.

Referring now to FIG. 1, a plastic substrate 10, suitably formed of a strip of polyethylene Lexan or other plastic sheet stock has punched therethrough a plurality of holes 12. Substrate 10 is suitably on the order of 0.2 inches thick, 3⅝ inches long and 1 1/16 inches wide. Indicator element means, such as thin filter paper discs 14 impregnated with a chemical which changes color in reaction to exposure to a given toxic gas (or gases), are disposed on one side of substrate 10 adjacent the holes or apertures 12 and maintained in alignment with the apertures by an adhesive backing 16. Backing 16 is suitably a pressure sensitive tape and preferably an adhesive metallic foil. An identification tab 18 can also be interposed between substrate 10 and backing 16. An adhesive strip 20 can be included, if desired, for mounting the dosage badge, for example, on the hat or sleeve of a firefighter. It should be appreciated that, in the alternative, the badge can, of course, cooperate with a separate holder or clip.

A cover sheet means 22, suitably a further strip of pressure sensitive tape (adhesive metallic foil) is disposed on the front surface of substrate 10, effectively enclosing the indicator discs 14. Cover sheet 22 also includes a non-adhesive pull-tab 24, suitably formed of common masking tape, to facilitate removal. The discs 14 are preferably of greater dimensions than the substrate apertures 12.

The filter paper discs 14 are thin, suitably on the order of a few thousandths of an inch to facilitate measurement of the dosage, that is, the integrated time-concentration exposure to the toxic gas. Plural discs impregnated with respective predetermined concentrations of indicator chemicals, such that the respective discs change color in response to varying dosage levels, can be provided. The indicator discs change color as a function of the amount of indicator chemical on the badge, the rate of transfer of the toxic gas to the badge surface and the length of exposure time. The transfer of gas to each indicator element means 14 is effected by diffusion from the atmosphere, which is in turn controlled by the diffusion coefficient of the gas and the concentration gradient of the gas in the atmosphere to which the badge is exposed. A thin disc 14, on the order of a few thousandths of an inch thick, is utilized such that the amount of adsorption of the gas (e.g., HCl) on the badge, if any, required to effect a reaction with the indicator chemical is small. Accordingly, where the atmosphere is constantly renewed, dosage becomes proportional to exposure time. At relative air/badge velocities below one mile per hour local gas concentration tends to be depleted by the badge, which gives rise to an erroneous dosage indication. However, one mile per hour is comparable to normal movement. Thus in field usage, normal movement and wind generally maintain the circulation above the one mile per hour point. Accordingly, a badge mounted on a person provides indicia of the concentration dosage to which the person is exposed.

A dosage badge in accordance with the present invention can be utilized to measure the dosage of any gas for which a color sensitive indicator is available and can react with a reagent. For example, a conventional indicator for carbon monoxide would be $PdCl_2$ test paper. A partial list of gases for which conventional indicators exist capable of being fabricated into apparatus according to the present invention, is provided in Table I. It is to be understood that the apparatus according to the present invention also may include as the indicator elements thereof means that are responsive to other environmental conditions besides the presence of a gas—for instance the presence of soot or other particulate contaminant, or the presence of various concentrations of different types of radiation.

TABLE I

Badge Detectable Gases

| | |
|---|---|
| Acetyline | Hydrogen Cyanide |
| Ammonia | Hydrogen Selenide |
| Arsine | Hydrogen Sulfide |
| Carbon Dioxide | Methyl Bromide |
| Carbon Monoxide | Methyl Mercaptan |
| Chlorine | Nickel Carbonyl |
| Chlorine Dioxide | Nitrogen Dioxide |
| Dimethyl Ether | Phosgene |
| Ethylene | Phosphine |
| Ethylene Oxide | Sulfur Dioxide |
| Vinyl Chloride | |

It should be appreciated that buffer solutions can be included on discs 14 to control dosage and glycol to inhibit evaporation and intensify the colors. For example, badges made utilizing $K_2CO_3$, sodium bicarbonite and glycerol solutions may be utilized.

Figure 2:
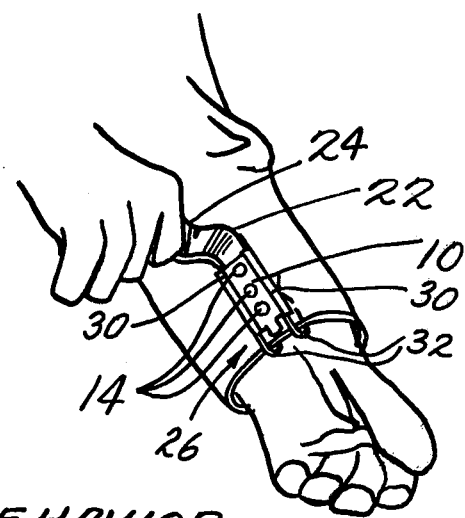
FIG. 2 is a pictorial illustration of the toxic gas dosage badge of FIG. 1.
Figure 3:
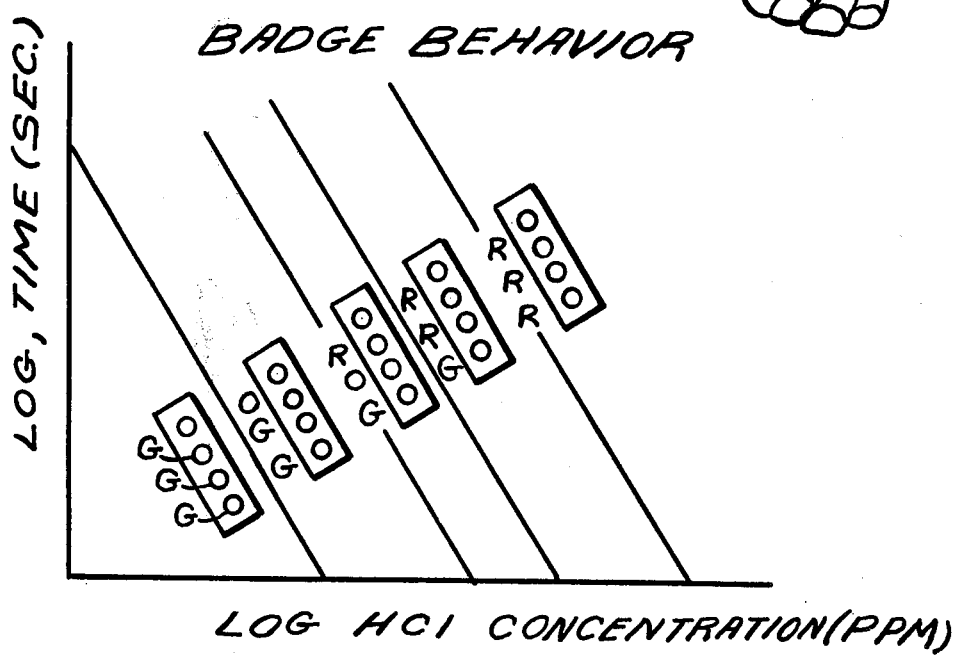
FIG. 3 is a pictorial graph of the response of a typical badge to various concentrations of a toxic chemical (HCl).

Dosage measurement is initiated by removing cover sheet 22 from the front of substrate 10 to expose indicator discs 14 to the atmosphere through apertures 12. Such action is illustrated pictorially in FIG. 2. The dosage badge is affixed to, for example, the sleeve of a fireman's overcoat, either by adhesive strip 20 or by a suitable clip or holder. An exemplary clip is shown at 26 in FIG. 2, having elongated edges 30 which support edges of the substrate 10, and having supporting clip loops 32 extending from one end of each of the edges 30 for engaging an article of clothing of the user, the non-adhesive pull tab 24 of the pressure sensitive tape 22 extending from an end of the substrate adjacent the ends of the edges 30 from which the supporting clip loops 32 extend so that the tape 22 may be readily removed from the substrate 10 while the entire indicating assembly (substrate 10, disks 14, and backing 16) remain attached to the user. Cover sheet 22 is easily removed by pulling on tab 24. Each of the respective discs 14 changes color in response to respective predetermined dosages of a chosen toxic gas, for example, HCl. As illustrated in FIG. 3, at low dosages, all of the indicator discs are of a first color, suitably green or blue. As the dosage increases, the colors of the indicators change, in sequence, from green to orange, and then from orange to red. The color changes in the badge, analogous to the color changes of a conventional stop light, are thus easy to read and interpret.

It should be appreciated that a dosage badge in accordance with the present invention is particularly advantageous in that it can be inexpensively fabricated. In preparing the badge, the substrate is first formed. A plastic strip is cut, holes are punched therethrough, and the substrate cleaned with alcohol. The adhesive backing strips are cut to length, and paper filter discs, suitably preimpregnated with a predetermined concentration of indicator chemical and buffer, are disposed in spaced relation on the adhesive side of the backing by, for example, an automatic dispenser. Similarly, an ID tab can be disposed on the backing. The backing strip is then applied to the substrate with the discs in alignment with the apertures in the substrate. The cover strips are then disposed on the front surface of the substrate, and the pull-tab attached and cut to length. It should be appreciated that unimpregnated filter paper discs can be set into the badge and loaded with indicator solution just prior to sealing the badge with the cover strip.

A three concentration indicator badge has been tested in laboratory conditions utilizing a universal indicator with a sodium bicarbonate buffer and glycerol water solution (to inhibit evaporation and improve color change contrast). Tests results indicate the badge response to be linear with dosage within 20% with air speed exceeding 1 mile per hour. Tests in the presence of a crib fire containing 300 grams of polyvinyl chloride provided dosage indications agreeing with concentrations measured by Dragger tube sampling. The color changes were found to be easily seen and interpreted by the firefighters at distances of 15 feet in a smokey atmosphere.

It will be understood that the above description is of illustrative embodiments of the present invention, and that the invention is not limited to the specific forms shown. For example, backings more rigid than the pressure sensitive tape described above, can be utilized if desired. Modifications may be made in the design and arrangements of the elements without departing from the spirit of the invention as defined in the appended claims.

What is claimed is:

1. Apparatus for indicating hazardous atmospheric conditions in a firefighting environment, consisting essentially of a substantially planar indicating assembly including a substrate having front and back surfaces, and having a plurality of apertures therein; a plurality of gas indicator elements, corresponding in number to the number of apertures in said substrate, each for indicating by color change the presence of respective predetermined time and concentration exposures to a gas, said gas indicator elements being of greater dimensions than said substrate strip apertures; backing means, adherent to said back surface of said substrate, for maintaining said indicator elements in aligned relationship with said substrate apertures; and a strip of pressure sensitive tape adhering to said front surface of said substrate for maintaining said indicator elements in a condition wherein they are not exposed to said hazardous atmospheric conditions, and so that upon removal of said tape said indicator elements are exposed to said hazardous atmospheric conditions, said tape having a non-adhesive pull tab at one end thereof; and means for attaching said indicating assembly to a user for use in detecting hazardous atmospheric conditions during firefighting, so that said pressure sensitive tape may be readily removed from said substrate while said indicating assembly remains attached to the user, said attaching means comprising a clip having elongated edges supporting edges of said substrate, and supporting clip loops extending from one end of each of said elongated edges for engaging an article of clothing of the user, said non-adhesive pull tab of said pressure sensitive tape extending from an end of said substrate adjacent the ends of said clip elongated edges from which said supporting clip loops extend.

2. Apparatus as recited in claim 1 wherein each of said indicator elements has a different responsiveness to time and concentration exposure to a particular gas in a hazardous atmosphere, so that said indicator elements change color in sequence.

3. Apparatus as recited in claim 1 wherein each of said indicator elements is capable of two differing color changes responsive to differing time and concentration exposures to a particular gas in a hazardous atmosphere.

4. Apparatus as recited in claim 1 wherein each of said indicator elements has a different responsiveness to time and concentration exposures to a particular gas in a hazardous atmosphere, so that said indicator elements change color in sequence, and wherein each of said indicator elements is capable of two different color changes responsive to differing time and concentration exposures to a particular gas in a hazardous atmosphere, each said indicator element originally being green, and then changing to orange after a predetermined time and concentration exposure to a particular gas in a hazardous atmosphere, and then changing to red after a further predetermined time and concentration exposure to a particular gas in a hazardous atmosphere.

5. Apparatus for indicating hazardous atmospheric conditions in a firefighting environment, comprising a substantially planar indicating assembly including a substrate having front and back surfaces, and having a plurality of apertures therein; a plurality of gas indicator elements, corresponding in number to the number of apertures in said substrate, each for indicating by color change the presence of respective predetermined time and concentration exposures to a gas; backing means adherent to said back surface of said substrate for maintaining said indicator elements in aligned relationship with said substrate apertures; and a strip of pressure sensitive tape adhering to said front surface of said substrate for maintaining said indicator elements in a condition wherein they are not exposed to said hazardous atmospheric conditions, and so that upon removal of said tape indicator elements are exposed to said hazardous atmospheric conditions, said tape having a non-adhesive pull tab at one end thereof; and means for attaching said indicating assembly to a user for use in detecting hazardous atmospheric conditions during firefighting, said means including a clip having elongated edges supporting edges of said substrate; and supporting clip loops extending from one end of each of said elongated edges for engaging an article of clothing of the user; said non-adhesive pull tab of said pressure sensitive tap extending from an end of said substrate adjacent the ends of said clip elongated edges from which the supporting clip loops extend.

* * * * *